United States Patent [19]

Marsh et al.

[11] 4,456,781

[45] Jun. 26, 1984

[54] CATALYTIC CONVERSION SYSTEM FOR OLIGOMERIZING OLEFINIC FEEDSTOCK TO PRODUCE HEAVIER HYDROCARBONS

[75] Inventors: Susan K. Marsh, Mt. Holly; Hartley Owen, Belle Mead; Bernard S. Wright, East Windsor, all of N.J.

[73] Assignee: Mobil Oil Corporation, New York, N.Y.

[21] Appl. No.: 488,823

[22] Filed: Apr. 26, 1983

[51] Int. Cl.³ .............................................. C07C 2/02
[52] U.S. Cl. ................................. 585/533; 585/502; 585/504
[58] Field of Search ........................ 585/502, 504, 533

[56] References Cited

U.S. PATENT DOCUMENTS

| | | | |
|---|---|---|---|
| 3,960,978 | 6/1976 | Givens et al. | 260/683 |
| 4,021,502 | 5/1977 | Plank et al. | 260/683 |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |

Primary Examiner—Curtis R. Davis
Attorney, Agent, or Firm—A. J. McKillop; M. G. Gilman; L. G. Wise

[57] ABSTRACT

A continuous catalytic process for oligomerizing lower olefins to heavier hydrocarbons wherein a continuous liquid olefinic feedstream is diluted with a liquid alkane stream, is improved by a technique which comprises cooling catalytically converted effluent, fractionating the effluent to obtain a condensed lower aliphatic recycle stream, a liquid $C_3$–$C_4$ product stream, a liquid product stream consisting essentially of $C_5$+ hydrocarbons and a gaseous $C_2$− gaseous stream by the sequential fractionation steps of: debutanizing the cooled effluent to obtain the liquid $C_5$+ hydrocarbon stream and a condensed lower aliphatic stream; de-ethanizing a portion of the lower aliphatic stream to recover gaseous offgas stream and a $C_3$–$C_4$ alkane product stream; and optionally recycling at least a portion of the condensed aliphatic stream from the debutanizing step for dilution of the olefinic feedstream.

13 Claims, 3 Drawing Figures

CATALYTIC CONVERSION SYSTEM FOR OLIGOMERIZING OLEFINIC FEEDSTOCK TO PRODUCE HEAVIER HYDROCARBONS

FIELD OF INVENTION

This invention relates to processes and apparatus for converting olefins to higher hydrocarbons, such as gasoline-range or distillate-range fuels. In particular it relates to techniques for operating a catalytic reactor system and effluent fractionation system.

BACKGROUND OF THE INVENTION

Developments in zeolite catalysts and hydrocarbon conversion processes have created interest in utilizing olefinic feedstocks, such as petroleum refinery streams rich in lower olefins, for producing $C_5+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing refinery streams that contain lower olefins, especially $C_2$–$C_5$ alkenes. This process may supplant conventional alkylation units. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over H-ZSM-5 is effective at moderately elevated temperatures and pressures. The conversion products are sought as liquid fuels, especially the $C_5+$ aliphatic and aromatic hydrocarbons. Olefinic gasoline is produced in good yield by the MOGD process and may be recovered as a product or recycled to the reactor system for further conversion to distillate-range products.

Olefinic feedstocks may be obtained from various sources, including fossil fuel processing streams, such as gas separation units, cracking of $C_2+$ hydrocarbons, coal byproducts, and various synthetic fuel processing streams. Cracking of ethane and conversion of conversion effluent is disclosed in U.S. Pat. No. 4,100,218 and conversion of ethane to aromatics over Ga-ZSM-5 is disclosed in U.S. Pat. No. 4,350,835. Olefinic effluent from fluidized catalytic cracking of gas oil or the like is a valuable source of olefins, mainly $C_3$–$C_4$ olefins, suitable for exothermic conversion according to the present MOGD process. The hot reactor effluent requires fractionation to recover the valuable distillate, gasoline and liquified $C_3$–$C_4$ (LPG) products. Conventional separation processes require expensive distillation towers to deethanize and further fractionate the various products.

In the past, this process has been carried out at elevated temperatures and pressures, requiring significant investment in furnaces, heat exchange equipment, compressors and pumps for the various feed streams, effluent and intermediate streams.

SUMMARY OF THE INVENTION

It is an object of the present invention to improve process economics by lowering equipment costs and increasing thermal efficiency in an olefin oligomerization system. This is achieved by a technique employing a fractionation sequence wherein hot reactor effluent is first separated into a light hydrocarbon stream ($C_4-$) and heavier hydrocarbon stream ($C_5+$) prior to deethanizing the reactor effluent. Hydrocarbon products include distillate, gasoline and LPG hydrocarbon in predetermined proportions.

A continuous process has been designed to achieve these objectives for an exothermic reactor system with efficient heat exchange, product recovery and recycle system. Advantageously, exothermic heat is recovered from the reactor effluent and utilized to heat one or more fractionation system liquid streams, such as a distillation tower reboiler stream.

Accordingly it is an object of the present invention to provide a continuous system for converting lower olefins to higher hydrocarbons such as gasoline or distillate wherein a continuous olefinic feedstream is diluted with a diluent stream. The improved technique comprises methods and means for cooling catalytically converted effluent, fractionating the effluent to obtain a condensed lower aliphatic stream rich in $C_3$–$C_4$ alkanes and a liquid product stream consisting essentially of $C_5+$ hydrocarbons by the sequential fractionation steps of (a) debutanizing the cooled effluent to obtain the liquid $C_5+$ hydrocarbon stream and a lower aliphatic overhead vapor stream;

(b) condensing and recycling at least a portion of the lower aliphatic stream; and (c) de-ethanizing a portion to said lower aliphatic stream to provide LPG product containing at least 80 mole % $C_3$–$C_4$ alkanes.

It has been found advantageous to provide a liquid lower alkane ($C_3$/$C_4$) and/or gasoline recycle stream as a diluent and to combine the liquid recycle and olefin feedstock at relatively lower pressure and pump the combined feedstream up to process pressure in the liquid phase. Substantial energy savings are achieved in this technique by single stage liquid pumping with subsequent heating to vaporize the combined olefinic feedstock and diluent stream prior to catalyst contact. By pressurizing and recycling a portion of the undeethanized condensed lower alkane stream for diluting the olefinic feedstream at process pressure, expensive fractionation can be avoided. The deethanizer tower can be outside the MOGD process loop and, advantageously a further step of combining a light hydrocarbon refinery stream with the lower aliphatic stream portion prior to de-ethanizing can be included in the deethanizing unit.

Typically, the olefinic stock consists essentially of $C_2$–$C_5$ aliphatic hydrocarbons containing a major fraction of monoalkenes in the essential absence of dienes or other deleterious materials. The process may employ various volatile lower olefins as feedstock, with oligomerization of $C_2$–$C_6$-olefins being preferred for either gasoline or distillate production. Preferably the olefinic feedstream contains about 50 to 75 mole % $C_3$–$C_5$ alkenes.

In one aspect of the system, the presssure reactor zone comprises a plurality of operatively-connected catalytic reactors arranged in a multi-stage serial flow, with interstage cooling of reactor effluent in the debutanizer reboiler section. The debutanizer reboiler section may include a plurality of reactor effluent cooling tubes combined in a common kettle-type reboiler shell.

These and other objects and features of the novel MOGD system will be seen in the following description of the drawing.

THE DRAWING

DESCRIPTION OF PREFERRED EMBODIMENTS

Figure 1:
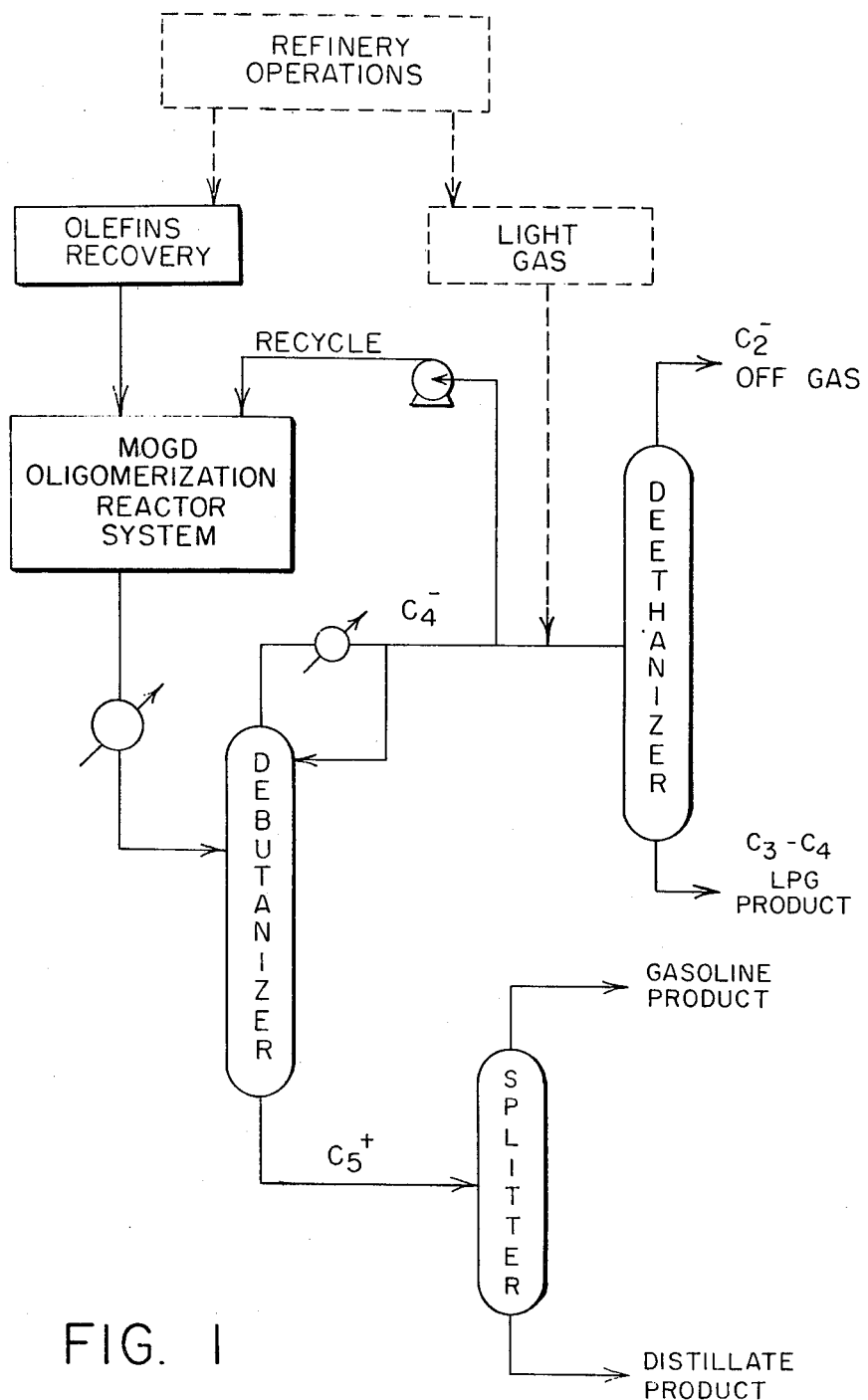
FIG. 1 is a simplified process flow diagram showing relationships between the major unit operations.

The overall relationship of the invention to a petroleum refinery is depicted in FIG. 1. Various olefinic and paraffinic light hydrocarbon streams may be involved in the reactor or fractionation subsystems. An olefinic feedstock, such as derived from catalytic cracker (FCC) effluent, may be employed as a feedstock rich in ethene, propene, butenes, etc. for the oligomerization reactor system 30. Cooled reactor effluent is fed to the fractionation sub-system for initial debutanizing in unit 40 to obtain a liquid $C_5+$ hydrocarbon stream and overhead vapor stream rich in lower alkanes, such as $C_1$ to $C_4$ paraffins. At least a portion of the debutanizer overhead is condensed by cooling under process pressure to provide tower reflux and reactor liquid recycle.

A portion of the debutanizer overhead stream is withdrawn from the MOGD plant loop for further fractionation in accordance with the present invention in de-ethanizer unit 50. Heavier hydrocarbon bottoms are separated into gasoline and distillate product streams in product splitter unit 60.

The fractionation sub-system has been devised to yield three main liquid product streams–LPG (mainly $C_3-C_4$ alkanes), gasoline boiling range hydrocarbons ($C_5$ to 330° F.) and distillate range heavier hydrocarbons (330° F.+). De-ethanizer off gas comprising methane and ethane with minor amounts of other light gases may be consumed within the MOGD system as furnace fuel gas, flared, or otherwise utilized.

While conventional refinery practice in fractionating hydrocarbon streams first provides for de-ethanizing the stream, followed by debutanizing and product splitting in sequence; it has been found to be advantageous in the present system to effect an initial fractionation of the entire MOGD reactor effluent to provide a light stream ($C_4-$) and a normally liquid $C_5+$ product stream. Ordinarily the reactor effluent is introduced to the initial fractionation unit as a mixed phase stream.

By operating the de-butanizer unit at adequate pressure to condense the overhead $C_4-$ vapors a liquid recycle stream can be fed to the MOGD reactor system with olefin feedstock. This condensed liquid stream can contain lower $C_1-C_2$ components as well as the liquid $C_3-C_4$ components, thus obviating the need for further fractionation of a significant portion of the de-butanizer overhead.

By placing the de-ethanizer unit outside the MOGD recycle loop, the cost of fractionating the offstream into liquid petroleum gas (LPG) and off gas can be reduced. The de-ethanizer function need not be dedicated to the olefins oligomerization plant, but may be integrated with other refinery streams, as shown in FIG. 1. Optionally, one or more light gas streams containing $C_1$ to $C_4$ aliphatic hydrocarbons may be combined with a non-recycled portion of the de-butanizer overhead for economic separation and recovery of the components. Existing de-ethanizing capacity may be employed, where the fractionation streams are compatible. Various heat exchange schemes are feasible within the inventive concept.

Figure 2:
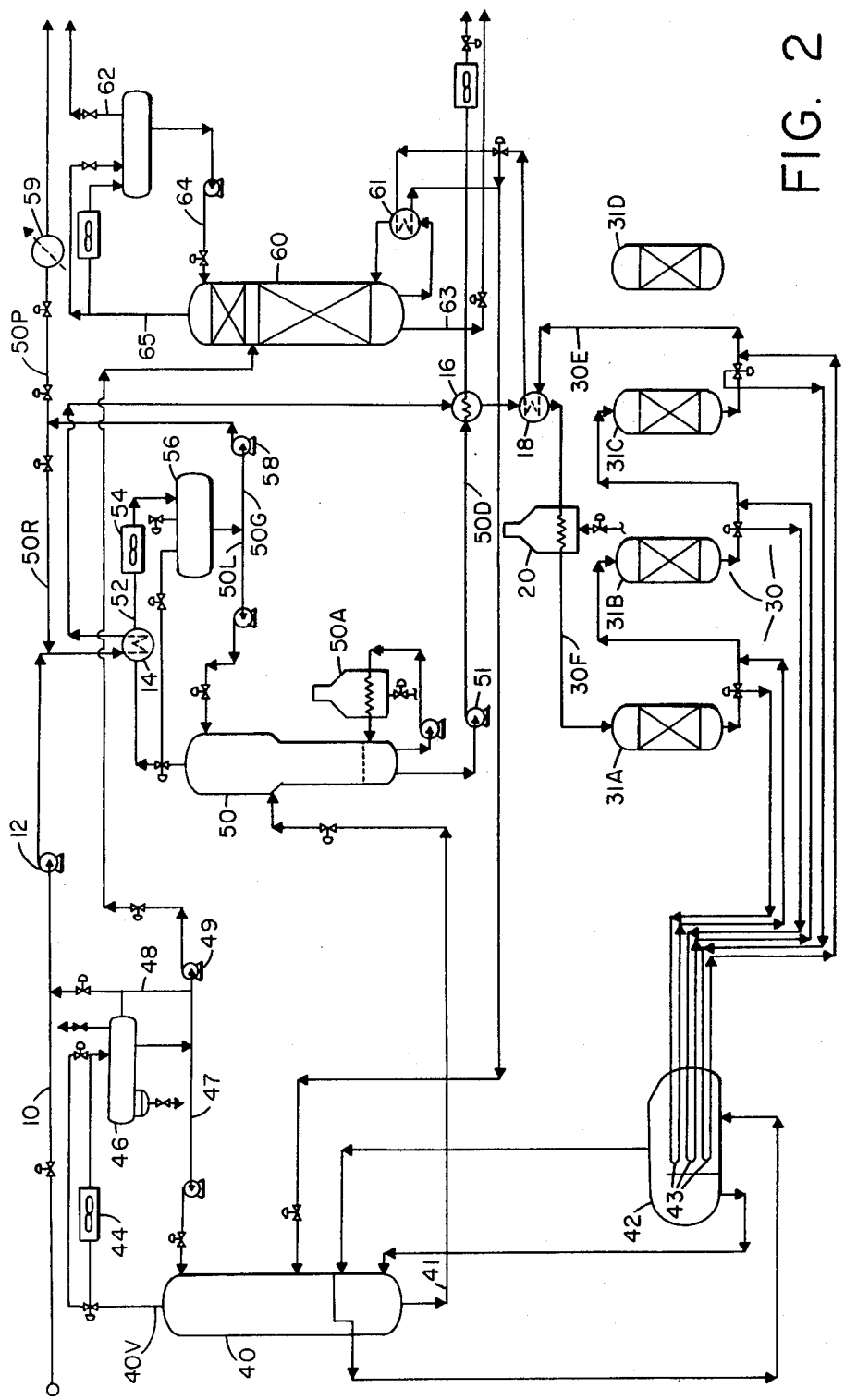
FIG. 2 is a schematic system diagram showing a process equipment and flow line configuration for a preferred embodiment.

The flow diagram of FIG. 2 of the drawing represents the overall process. The olefinic feedstock is usually supplied as a liquid stream under moderate superatmospheric pressure and warm ambient temperature. Ordinarily, the feedstock is substantially below the process reactor pressure, and may be combined with recycled liquid diluent which is rich in $C_3-C_4$ alkanes at similar temperature and pressure. Following pressurization of the combined olefin-recycle and/or gasoline feedstreams, it is passed through the catalytic reactor system, which includes multiple fixed bed reactors operatively connected with the heat exchange system, as described later. The reactor effluent may be cooled by heat exchange with a debutanizer bottoms fraction. A condensed debutanizer overhead stream is recovered for recycle and the heavier hydrocarbons obtained by oligomerization of the feedstock is fractionated in a product splitter unit to yield a distillate fraction (330° F.+ boiling point) and a gasoline fraction (boiling range of 125° F. to 330° F.) in varying amount.

Since the gasoline product comprises a major fraction of unsaturated aliphatic liquid hydrocarbons, it may be recovered and hydrotreated to produce spark-ignited motor fuel if desired. Optionally, all or a portion of the olefinic gasoline range hydrocarbons from the splitter unit may be recycled for further conversion to heavier hydrocarbons in the distillate range. This may be accomplished by combining the recycle gasoline with lower olefin feedstock and diluent prior to heating the combined streams.

Process conditions, catalysts and equipment suitable for use in the MOGD process are described in U.S. Pat. Nos. 3,960,978 (Givens et al), 4,021,502 (Plank et al), and 4,150,062 (Garwood et al). Hydrotreating and recycle of olefinic gasoline are disclosed in U.S. Pat. No. 4,211,640 (Garwood and Lee). Other pertinent disclosures include U.S. Pat. No. 4,227,992 (Garwood and Lee) and U.S. patent application No. 108,617, filed Dec. 31, 1979 (Dwyer and Garwood) relating to catalytic processes for converting olefins to gasoline/distillate. The above disclosures are incorporated herein by reference.

Catalyst

The catalyst materials suitable for use herein are effective in oligomerizing lower olefins, especially propene and butene-1 to higher hydrocarbons. The unique characteristics of the acid ZSM-5 catalysts are particularly suitable for use in the MOGD system. Effective catalysts include those zeolites disclosed in U.S. patent application Ser. No. 390,099 filed June 21, 1982 (Wong and LaPierre) and Application Ser. No. 408,954 filed Aug. 17, 1982 (Koenig and Degnan), which relate to conversion of olefins over large pore zeolites. A preferred catalyst material for use herein is an extrudate (1.5 mm) comprising 65 weight % HZSM-5 and 35% alumina binder, having an acid cracking activity ($\alpha$) of about 160 to 200.

The members of the class of crystalline zeolites for use in this invention are characterized by a pore dimension greater than about 5 Angstroms, i.e., it is capable of sorbing paraffins having a single methyl branch as well as normal paraffins, and it has a silica to alumina mole ratio of at least 12.

Although such crystalline zeolites with a silica to alumina mole ratio of at least about 12 are useful, it is preferred to use zeolites having higher ratios of at least about 30. In some zeolites, the upper limit of silia to alumina mole ratio is unbounded, with values of 30,000 and greater.

The members of the class of zeolites for use herein are exemplified by ZSM-5, ZSM-5/ZSM-11 intermediate, ZSM-11, ZSM-12, ZSM-23, ZSM-35, ZSM-38, ZSM-48 and other similar materials. U.S. Pat. No. 3,702,886 describing and claiming ZSM-5 is incorporated herein by reference. Also, Re. No. 29,948 describing and claiming a crystalline material with an X-ray diffraction pattern of ZSM-5, is incorporated herein by reference as is U.S. Pat. No. 4,061,724 describing a high silica ZSM-5 referred to as "silicate" in such patent. The ZSM-5/ZSM-11 intermediate is described in U.S. Pat. No. 4,229,424. ZSM-11 is described in U.S. Pat. Nos. 3,709,979. ZSM-12 is described in U.S. Pat. No. 3,832,449. ZSM-23 is described in U.S. Pat. No. 4,076,842. ZSM-35 is described in U.S. Pat. 4,016,245. ZSM-38 is described in U.S. Pat. No. 4,046,859. The entire contents of the above identified patents are incorporated herein by reference. ZSM-48 is more particularly described in U.S. patent application Ser. No. 343,131 filed Jan. 27, 1982, the entire contents of which are incorporated herein by reference.

The zeolites used in additive catalysts in this invention may be in hydrogen form or they may be base exchanged or impregnated to contain a rare earth cation complement. Such rare earth cations comprise Sm, Nd, Pr, Ce and La. It is desirable to calcine the zeolite after base exchange.

The catalyst and separate additive composition for use in this invention may be prepared in various ways. They may be separately prepared in the form of particles such as pellets or extrudates, for example, and simply mixed in the required proportions. The particle size of the individual component particles may be quite small, for example from about 10 to about 150 microns, when intended for use in fluid bed operation, or they may be as large as up to about 1–10 mm for fixed bed operation. The components may be mixed as powders and formed into pellets or extrudate, each pellet containing both components in substantially the required proportions. It is desirable to incorporate the zeolite component of the separate additive composition in a matrix. Such matrix is useful as a binder and imparts greater resistance to the catalyst for the severe temperature, pressure and velocity conditions encountered in many cracking processes. Matrix materials include both synthetic and natural substances. Such substances include clays, silica and/or metal oxides. The latter may be either naturally occurring or in the form of gelatinous precipitates, sols or gels including mixtures of silica and metal oxides. Frequently, zeolite materials have been incorporated into naturally occurring clays, e.g. bentonite and kaolin.

A particularly advantageous form of the catalyst is an extruded pellet having a diameter of about 1-3 mm, made by mixing steamed zeolite crystals eg. silica:alumina=70:1–500:1 with α-alumina monohydrate in a proportion of about 2:1 and calcining the formed material to obtain an extrudate having a void fraction of about 30–40%, preferably about 36%.

General Process Description

Referring to FIG. 2, olefinic feedstock is supplied to the MOGD plant through liquid conduit 10 under steady stream conditions, diluted and pressurized to process pressure by pump 12. The olefinic feedstock plus recycled liquids are then sequentially heated by passing through indirect heat exchange units 14, 16, 18 and furnace 20 to achieve the temperature for catalytic conversion in reactor system 30, including plural reactor vessels 31A, B, C, etc.

The reactor system section shown consists of 3 downflow fixed bed, series reactors on line with exchanger cooling between reactors. The reactor configuration allows for any reactor to be in any position, A, B or C.

The reactor in position A has the most aged catalyst and the reactor in position C has freshly regenerated catalyst. The cooled reactor effluent is fractionated first in a debutanizer 40 to provide lower aliphatic liquid recycle and then in splitter unit 50 which not only separates the debutanizer bottoms into gasoline and distillate products but provides liquid gasoline recycle.

The gasoline recycle is not only necessary to produce the proper distillate quality but also (with the non-olefins in the feed and $C_3$–$C_4$ lower alkane recycle) limits the exothermic rise in temperature across each reactor to less than 30° C. However, the reactor T's are also a function of the $C_3$–$C_4$ recycle flow rate. Change in recycle flow rate is intended primarily to compensate for gross changes in the feed non-olefin flow rate. As a result of preheat, the liquid recycles are substantially vaporized by the time that they reach the reactor inlet. The following is a description of the process flow in detail.

Olefin feedstock under flow control is combined in conduit 10 with condensed $C_3$–$C_4$ rich recycle, which is also under flow control. The resultant stream is pumped up to system pressure by pump 12 and is combined with gasoline recycle after that stream has been pumped up to system pressure by pump 58. The combined stream (feed plus recycle plus gasoline recycle) after preheat is routed to the inlet 30F of the reactor 31A of system 30. The combined stream (herein designated as the reactor feed stream) is first preheated against the splitter tower 50 overhead in exchanger 14 (reactor feed/splitter tower overhead exchange) and then against the splitter tower bottoms in exchanger 16 (reactor feed/splitter bottoms exchanger) and then finally against the effluent from the reactor in position C, in exchanger 18 (reactor feed/reactor effluent exchanger). In the furnace 20, the reactor feed is heated to the required inlet temperature for the reactor in position A.

Because the reaction is exothermic, the effluents from the reactors in the first two positions A, B are cooled to the temperature required at the inlet of the reactors in the last two positions, B, C, by partially reboiling the debutanizer, 40. Temperature control is accomplished by allowing part of the reactor effluents to bypass the reboiler 42. Under temperature control of the bottom stage of the debutanizer, the additional required reboiling is provided by part of the effluent from the reactor 31 in position C.

After preheating the reactor feed, the reactor effluent reboils deethanizer bottoms 61 and is then routed as a mixed phase stream 80+% vapor to the debutanizer which is operated at a pressure which completely condenses the debutanizer tower overhead 40V by cooling in condenser 44. The liquid from debutanizer overhead accumulator 46 provides the tower reflux 47, the lower alkane recycle 48 and feed to the deethanizer 60, which, after being pumped to the deethanizer pressure by pump 49 is sent to the deethanizer 60. The deethanizer accumulator overhead 65 is routed to the fuel gas system 62. The accumulator liquid 64 provides the tower reflux. The bottoms stream 63 (LPG product) may be sent to an unsaturated gas plant or otherwise recovered.

The bottoms stream 41 from the debutanizer 40 is sent directly to the splitter, 50 which splits the $C_5+$ material into $C_5+330°$ F. gasoline (overhead liquid product and recycle) and 330° F.+ distillate (bottoms product). The splitter tower overhead stream 52, after preheating the reactor feed stream is totally condensed in the splitter tower overhead condenser 54. The liquid from the overhead accumulator 56 provides the tower reflux 50L, the gasoline product 50P and the specified gasoline recycle 50R under flow control. For example, 1 mole gasoline/mole olefin in feed is pressurized by pump 58 for recycle. After being cooled in the gasoline product cooler 59, the gasoline product is sent to the gasoline pool. The splitter bottoms fraction is pumped to the required pressure by pump 51 and then preheats the reactor feed stream in exchanger 16. Finally, the distillate product 50D is cooled to ambient temperature before being hydrotreated to improve its cetane number.

From an energy conservation standpoint, it is advantageous to reboil the debutanizer using all three reactor effluents as opposed to using a fired reboiler. A kettle reboiler 42 containing 3 U-tube exchangers 43 in which the reactor 31 effluents are circulated is a desirable feature of the system. Liquid from the bottom stage of debutanizer 40 is circulated in the shell side. Alternatively three thermosyphon reboilers in series would suffer the disadvantages of a large pressure drop and control problems inherent in the instability resulting from the tower bottoms being successively vaporized in each reboiler. Although the pressure drop problem would be overcome with three reboilers in parallel, there would be considerable difficulty in controlling the allocation of tower bottoms to each parallel reboiler.

In order to provide the desired quality and rate for both liquid lower alkane ($C_3-C_4$) and gasoline recycles, it is necessary to fractionate the reactor effluent. Phase separators do not give the proper separation of the reactor effluent to meet the quality standards and rate for both liquid recycles. For example, the gasoline recycle would carry too much distillate and lights, while the $C_3-C_4$ recycle would contain gasoline boiling cuts. Consequently, it would be difficult to properly control the liquid recycles if separators were employed. In prior refinery practice, it was customary to deethanize a stream to remove very low molecular weight components prior to further fractionation to recover the $C_3-C_4$ gasoline and distillate streams. However, such prior practice would involve significantly greater equipment cost and poor energy conservation. It is a feature of the present system that the cooled reactor effluent is first fractionated in an efficient debutanizer unit to provide a condensed liquid stream rich in $C_3-C_4$ alkanes, part of which is recycled and part of which is deethanized to provide fuel gas and LPG product.

The deethanizer fractionation unit 60 may be a tray-type design or packed column, with about 13 to 18 theoretical stages being provided for optimum LPG product. With proper feedtray locations between 3 and 7 trays from the top, 15 theoretical stages in the deethanizer are adequate to assure proper fractionation. The deethanizer tower diameter, related fractionation equipment and heat exchange area are reduced considerably from conventional systems by reason of the prior debutanizing and withdrawing condensed light hydrocarbon for recycle. Since the deethanizer unit is operated at a significantly higher pressure (eg. 10–15 atmospheres) than the debutanizer or splitter columns, pumping energy is significantly reduced with a small mass flow rate.

The product splitter fractionation unit 50 receives the debutanizer bottoms, preferably as a mixed phase stream containing a major fraction of vapor (eg. 70 weight %) The main splitter column may be a tray-type or packed vertical fractionating column, with a furnace fixed bottoms reboiler 50A and gasoline reflux loop 14, 52, 54, 56, 50B. The splitter distillation tower 50 is preferably operated at substantially atmospheric pressure to avoid excessive bottoms temperature, which might be deleterious to the distillate product. The fractionation equipment and operating techniques are substantially similar for each of the major stills 40, 50, 60, with conventional plate design, reflux and reboiler components. The fractionation sequence and heat exchange features of the present system are operatively connected in an efficient MOGD system provide significant economic advantages.

By comparison with conventional fractionation systems wherein the entire reactor effluent would be first deethanized and then debutanized and split into $C_5+$ gasoline or distillate fractions; the present fractionation system requires fewer overall theoretical stages in the total distillation tower complex.

MOGD operating modes may be selected to provide maximum distillate product by gasoline recycle and optimal reactor system conditions; however, it may be desired to increase the output of gasoline by decreasing or eliminating the gasoline recycle. Operating examples are given for both the distillate mode and gasoline mode of operation, utilizing as the olefinic feedstock a pressurized stream FCC olefinic effluent (about 1200 kPa) comprising a major weight and mole fraction of $C_3=/C_4=$, as set forth in Table I. The adiabatic exothermic oligomerization reaction conditions are readily optimized at elevated temperature and/or pressure to increase distillate yield or gasoline yield as desired, using H-ZSM-5 type catalyst. Particular process parameters such as space velocity, maximum exothermic temperature rise, etc. may be optimized for the specific oligomerization catalyst employed, olefinic feedstock and desired product distribution.

Distillate Mode Operations

A typical distillate mode multi-zone reactor system employs inter-zone cooling, whereby the reaction exotherm can be carefully controlled to prevent excessive temperature above the normal moderate range of about 190° to 315° C. (375°–600° F.).

Advantageously, the maximum temperature differential across any one reactor is about 30° C. ($\Delta T \sim 50°$ F.) and the space velocity (LHSV based on olefin feed) is about 0.5 to 1. Heat exchangers provide inter-reactor cooling and reduce the effluent to fractionation temperature. It is an important aspect of energy conservation in the MOGD system to utilize at least a portion of the reactor exotherm heat value by exchanging hot reactor effluent from one or more reactors with a fractionator stream to vaporize a liquid hydrocarbon distillation tower stream, such as the debutanizer reboiler. Optional heat exchangers may recover heat from the effluent stream prior to fractionation. Gasoline from the recycle conduit is pressurized by pump means and combined with feedstock, preferably at a mole ratio of about 1–2 moles per mole of olefin in the feedstock.

It is preferred to operate in the distillate mode at elevated pressure of about 4200 to 7000 kPa (600–1000 psig). A typical material balance for distillate mode operation is given in Table I.

TABLE I

STREAM COMPONENTS MOLE % - DISTILLATE MODE

| Stream Component | Feedstock (Fresh Olefins) | Liquid $C_3$-$C_4$ Recycle | Gasoline Recycle/ Product | Reactor Feedstream | Reactor Effluent | Debutanizer Bottoms | Deethanizer Overhead | Deethanizer Reflux | Deethanizer Off-Gas (Fuel) | Deethanizer Bottoms (LPG) |
|---|---|---|---|---|---|---|---|---|---|---|
| $C_1$ | 0 | 0.27 | 0 | .04 | .12 | 0 | .76 | .32 | 3.39 | 0 |
| $C_2^=$ | .12 | .13 | 0 | .08 | .06 | 0 | .68 | .51 | 1.66 | 0 |
| $C_2$ | 1.04 | 2.52 | 0 | .88 | 1.15 | 0 | 16.54 | 13.95 | 32.08 | 0 |
| $C_3^=$ | 31.93 | 3.47 | 0 | 15.70 | 1.58 | 0 | 11.48 | 11.66 | 10.40 | 2.88 |
| $C_3$ | 11.98 | 29.92 | 0 | 10.25 | 13.61 | 0 | 61.12 | 63.16 | 48.9 | 28.27 |
| $iC_4$ | 17.61 | 40.34 | .22 | 14.60 | 18.46 | .20 | 7.26 | 7.99 | 2.85 | 43.54 |
| $C_4^=$ | 31.81 | 10.36 | .15 | 16.75 | 4.78 | .13 | 1.23 | 1.37 | .43 | 11.21 |
| $nC_4$ | 4.80 | 12.49 | .54 | 4.38 | 5.94 | .47 | .92 | 1.03 | .28 | 13.53 |
| $iC_5$ | .39 | .34 | 10.64 | 4.20 | 5.31 | 9.36 | 0 | 0 | 0 | .37 |
| $C_5^=$ | .30 | .17 | 9.56 | 3.72 | 4.65 | 8.4 | 0 | 0 | 0 | .18 |
| $nC_5$ | .01 | 0 | .52 | .20 | .25 | .46 | 0 | 0 | 0 | 0 |
| Gasoline | 0 | 0 | 75.38 | 28.08 | 36.3 | 66.62 | 0 | 0 | 0 | 0 |
| Distillate | 0 | 0 | 2.99 | 1.11 | 7.83 | 14.37 | 0 | 0 | 0 | 0 |
| $H_2O$ | .01 | 0 | 0 | .01 | .01 | 0 | 0 | 0 | 0 | 0 |
| Mass Flow | 100 | 33.3 | 160.4 | 293.7 | 293.7 | 212.6 | 21.3 | 18.5 | 2.8 | 45.1 |
| Stream No. (FIG. 2) | 10 | 48 | 50G | 30F | 30E | 41 | 65 | 64 | 62 | 63 |

The mass flow rate relative to the major process streams for a preferred distillate-optimized MOGD plant are given in Table II, along with process temperature and pressure conditions. The mass flow rate at steady state is expressed in part by weight per 100 parts of fresh feed.

TABLE II

| Process Stream/No. | Mass Flow Rate | Temperature (°C.) | Pressure kPa(a) (Kilo Pascals) absolute |
|---|---|---|---|
| Feedstock/10 | 100 | 38 | 1205 |
| $C_3$-$C_4$ recycle/48 | 33.3 | 43 | 1010 |
| Gasoline recycle/59 | 160.4 | 65 | — |
| Reactor Feed/30F | 293.7 | 232/271* | 4200 |
| Reactor effluent/30E | 293.7 | 236/259* | 3686 |
| Debut. overhead/40V | 183.9 | 61 | 1050 |
| Debut. reflux/47 | 102.9 | — | 1015 |
| Debut. over. prod./48 | 81.1 | 43 | 1015 |
| Debut. bottoms/41 | 212.6 | 197 | 1100 |
| Deeth. feed/60F | 47.8 | 43 | 2140 |
| Deeth. overhead/65 | 21.3 | 58 | 2100 |
| Deeth. reflux/64 | 18.5 | 43 | — |
| Deeth. off gas/62 | 2.8 | 43 | 2070 |
| LPG Prod./63 | 45.1 | 91 | 2110 |
| Splitter overhead/52 | 196.6 | 124 | 160 |
| Splitter reflux/50B | 28.3 | 65 | 105 |
| Splitter Product/50G | 168.3 | 65 | 105 |
| Gasoline Product/50P | 8 | 43 | 790 |
| Distillate Product/50D | 44.3 | 43 | 970 |

*SOC/EOC

The gasoline product is recovered from this mode of operation at the rate of 8% of olefinic feedstock, whereas distillate is recovered at 44% rate. Product properties are shown in Table III.

TABLE III

| PRODUCT PROPERTIES | | |
|---|---|---|
| Properties | Gasoline $C_6$-330° F. | Distillate 330° F. + (RAW) |
| Gravity, °API | 62.8 | 48.5 |
| Total Sulfur, ppmw | 0 | 0 |
| Octane Number, R + O | 90 | — |
| Bromine Number | — | 78.9 |
| Weight % $H_2$ | — | 14.3 |
| Aniline Pt | — | 163 |
| Freeze Pt (°F.) | — | <−76 |
| Cetane Number | — | 33 |
| Luminometer Number | — | 69 |
| ASTM Distillation | D-86 | D-1160 |
| IBP | 165 | 348 |
| 10/30 | 217/252 | 379/407 |
| 50/70 | 284/316 | 449/511 |
| 90 | 414 | 676 |
| 95 | — | 770 |
| EP | 531 | |

The reactor system contains multiple downflow adiabatic catalytic zones in each reactor vessel. The liquid hourly space velocity (based on total fresh feedstock) is about 1 LHSV. In the distillate mode the inlet pressure to the first reactor is about 4200 kPa (600 psig total), with an olefin partial pressure of at least about 1200 kPa. Based on olefin conversion of 50% for ethene, 95% for propene, 85% for butene-1 and 75% for pentene-1, and exothermic heat of reaction is estimated at 450 BTU per pound of olefins converted. When released uniformly over the reactor beds, a maximum ΔT in each reactor is about 30° C. In the distilate mode the molar recycle ratio for gasoline is equimolar based on olefins in the feedstock, and the $C_3$-$C_4$ molar recycle is 0.5:1.

From the olefinic feedstock, which contains about 62% olefins, the distillate mode operation described produces about 31 vol. % distillate along with about 6.3% gasoline, 6% LPG and 38+% unconverted olefins and saturated aliphatics in the feed.

Gasoline Mode Operation

By way of comparison, the distillate mode is compared with operation of the same system shown in FIG. 2, except that the reactor system is operated at relatively elevated temperature and moderate pressure with no gasoline recycle. The distillate yield is reduced to about 13 vol. % and the gasoline yield increased to about 27%.

The gasoline mode reactor is operated at the higher conversion temperature and does not require maximum differential temperature control closer than about 65° C. ($\Delta T \sim 120°$ F.) in the approximate elevated range of 230° to 375° C. (450°-700° F.). The reactor bed is maintained at a moderate superatmospheric pressure of about 400 to 3000 kPa (50-400 psig), and the space velocity for ZSM-5 catalyst to optimize gasoline production should be about 0.5 to 2 (LHSV). Preferably, all of the catalyst reactor zones in the system comprise a fixed bed down flow pressurized reactor having a porous bed of ZSM-5 type catalyst particles with an acid activity of about 160 to 200, identical with the distillate mode system for simplifying mode selection and cyclic operation.

By comparison with the distillate mode examples, the gasoline mode system is operated at the same space velocity (LHSV=1, based on total fresh feed), maximum allowable temperature rise ($\Delta T \sim 28°$ C.), catalyst aging rates and elevated temperature (SOC=230° C. min., EOC=295° C. max.). Total reactor pressure is reduced to 2160 kPa (300 psig), with a minimum olefin partial pressure at reactor inlet of about 350 kPa (50 psia). In the gasoline mode the exothermic heat of reaction is reduced from 450 to 380 BTU/pound of olefins converted. Since the gasoline recycle is reduced from equimolar amounts with the olefins to nil, the $C_3-C_4$ recycle mol ratio is increased from about 0.5:1 to 2:1 to provide adequate diluent. Under the stated gasoline mode conditions ethylene conversion is about 50%, propene, 95%; butene-1, 85%; and pentene-1, 75%. On a weight percent basis the gasoline ($C_6$-330° F.) yield is 52.4% with 32% distillate (330° F.+), as compared to 12.6 weight % and 79%, respectively in the distillate mode.

Heat integration and fractionation techniques may be adapted to accommodate optional distillate or gasoline modes. The combined olefin/$C_3-C_4$ recycle feedstream may be preheated by debutanizer bottoms in an optional exchanger. Additional pump capacity may be required to handle increased recycle liquid.

Preferably the ZSM-5 catalyst is kept on stream until the coke content increases from 0% at the start of cycle (SOC) until it reaches a maximum of 30 weight % at end of cycle (EOC) at which time it is regenerated by oxidation of the coke deposits. Typically a 30-day total cycle can be expected between regenerations. The reaction operating temperature depends upon its serial position. The system is operated advantageously (as shown in FIG. 2) by increasing the operating temperature of the first reactor (Position A) from about 230° C.-255° C. (SOC) to about 270° C.-295° C. (EOC) at a catalyst aging rate of 3°-6° C./day. Reactors in the second and subsequent positions (B, C, etc.) are operated at the same SOC temperature; however, the lower aging rate (eg.-3° C./day) in continuous operation yields a lower EOC maximum temperature (eg.-about 275° C.), after about 7 days on stream. The end of cycle is signalled when the outlet temperature of the reactor in position A reaches its allowable maximum. At this time the inlet temperature is reduced to start of cycle levels in order to avoid excessive coking over the freshly regenerated catalyst when reactor 31D is brought on-line, after having been brought up to reaction pressure with an effluent slip stream.

Regeneration of coked catalyst may be effected by any of several procedures. The catalyst may be removed from the reactor of the regeneration treatment to remove carbonaceous deposits or the catalyst may be regenerated in-situ in the reactor.

It is preferred to have at least three adiabatic reactors in continuous service; however, the $\Delta T$ becomes smaller with increased numbers of serial reactors and difficulties may be encountered in exploiting the reaction exotherm for reboiling the debutanizer unit and preheating reactor feed. A smaller number of serial reactors in the system would require much greater $C_3-C_4$ recycle to control the reaction exotherms from catalytic oligomerization.

Individual reactor vessels should be sized to accommodate the fixed catalyst bed with a normal pressure drop of about 100 kPa (15 psi) and total mass flow rate of about 3600 lbs/hr. $-\text{ft.}^2$. A typical vessel is constructed of steel or steel alloy to withstand process pressure up to about 70 atmospheres (7000 kPa) at maximum operating temperature. An enclosed cylindrical vessel with L/D ratio of about 2:1-10:1, preferably 4:1 to 6:1, is satisfactory. Since the reactor feed stream is completely vaporized or contains a minor amount of hydrocarbon liquid, no special feed distributor internal structure is required to obtain substantially uniform downward flow across the catalyst bed.

Alternative Design

Figure 3:
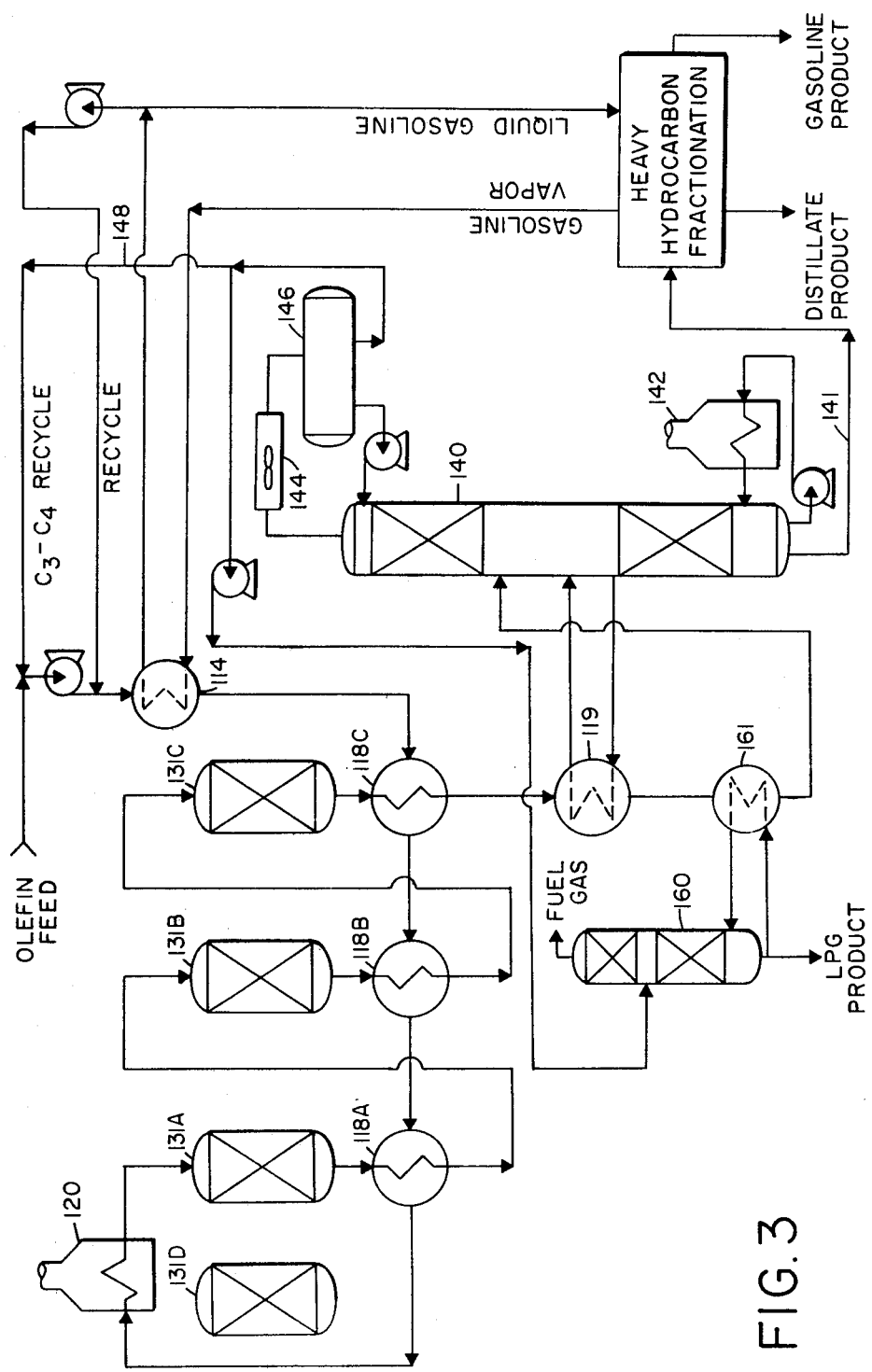
FIG. 3 is an alternative reactor system flow diagram.

An alternative technique for operating a MOGD plant is shown in FIG. 3, which employs $C_3-C_4$ recycle 148 for diluting the olefin feedstock. The combined reactor feedstream is heated indirectly by fractionator overhead gasoline vapor in exchanger unit 114 and passed sequentially through reactor effluent exchangers 118C, 118B, 118A and furnace 120 before entering catalytic reactors 131 A, B, C. Heat is exchanged between debutanizer 140 and hot reactor effluent in exchanger 119 to vaporize a lower tower fraction rich in $C_5+$ hydrocarbons. The debutanizer bottoms are withdrawn through $C_5+$ product line 141 and reboiled by furnace 142. Light gases from the debutanizer 140 are condensed in air cooler 144 and separated in accumulator 146 for reflux and recycle. A portion of the condensed light hydrocarbon stream is deethanized in tower 160 to provide fuel off gas and LPG product. The liquid from the bottom stage is reboiled by reactor effluent in exchanger 161 to recover additional heat values and to partially condense the heavier hydrocarbon in the effluent prior to debutanizing.

While the novel system has been described by reference to particular embodiments, there is no intent to limit the inventive concept except as set forth in the following claims.

What is claimed is:

1. In a continuous catalytic process for oligomerizing lower olefins to heavier hydrocarbons wherein a continuous liquid olefinic feedstream is diluted with a liquid alkane stream and contracted with oligomerization catalyst, the improvement which comprises:

cooling catalytically converted effluent, fractionating the effluent to obtain a condensed lower aliphatic recycle stream, a liquid $C_3-C_4$ product stream, a liquid product stream consisting essentially of $C_5+$ hydrocarbons and a gaseous $C_2-$ gaseous stream by the sequential fractionation steps of debutanizing the cooled effluent to obtain the liquid $C_5+$ hydrocarbon stream and condensed lower aliphatic stream;

de-ethanizing a portion of the lower aliphatic stream to recover gaseous ethane stream and a $C_3$–$C_4$ alkane product stream; and recycling at least a portion of the condensed aliphatic stream from the debutanizing step for dilution of the olefinic feedstream.

2. In a continuous catalytic process according to claim 1, the further step of fractionating the liquid $C_5+$ product stream into a gasoline range hydrocarbon stream and a distillate range hydrocarbon stream.

3. In a continuous catalytic process according to claim 2, the further step of recycling at least a portion of liquid gasoline range olefinic hydrocarbons to combine with the liquid olefin feedstream.

4. In a continuous catalytic process for converting olefins to gasoline or diesel fuel wherein a continuous olefinic feedstream is diluted with a diluent stream and contracted with oligomerization catalyst, the improvement which comprises:

cooling catalytically converted effluent, fractionating the effluent to obtain a condensed lower aliphatic stream rich in $C_3$–$C_4$ alkanes and a liquid product stream consisting essentially of $C_5+$ hydrocarbons by the sequential fractionation steps of (a) debutanizing the cooled effluent to obtain the liquid $C_5+$ hydrocarbon stream and a lower aliphatic overhead vapor stream;

(b) condensing and recycling at least a portion of the lower aliphatic stream; and (c) de-ethanizing a portion of said lower aliphatic stream to provide LPG product containing at least 80 mole % $C_3$–$C_4$ alkanes.

5. The process of claim 4 including the steps of pressurizing and recycling at least a portion of unde-ethanized condensed lower alkane stream for diluting the olefinic feedstream at process pressure.

6. The process of claim 4 comprising the further step of combining a light hydrocarbon refinery stream with the lower aliphatic stream portion prior to de-ethanizing.

7. The process of claim 4 which comprises the further steps of at least partially cooling catalytic reactor effluent sequentially by heat exchange with reactor feed stock and by reboiling liquid de-ethanizer tower bottoms.

8. The process of claim 4 wherein substantially the entire de-butanizer overhead vapor stream is condensed prior to recycle and de-ethanizing.

9. The process of claim 4 wherein said oligomerization catalyst comprises acid zeolite characterized by a pore dimension greater than about 5 Angstroms.

10. The process of claim 3 wherein said zeolite has a silica to alumina mole ratio of at least 12.

11. The process of claim 10 wherein said zeolite consists essentially of acid ZSM-5.

12. The process of claim 10 wherein said zeolite has an acid cracking activity of about 160 to 200.

13. The process of claim 4 wherein substantially all LPG product from de-ethanizing is recovered as product of the process.

* * * * *

UNITED STATES PATENT AND TRADEMARK OFFICE
CERTIFICATE OF CORRECTION

PATENT NO. : 4,456,781
DATED : June 26, 1984
INVENTOR(S) : S.K. Marsh, H. Owen, B.S. Wright It is certified that error appears in the above-identified patent and that said Letters Patent is hereby corrected as shown below:

Col. 12, Claim 1, line 58    contracted should be --contacted--.
Col. 13, Claim 4, line 20    contracted should be --contacted--.
Col. 14, Claim 10, line 23   "3" should be --9--.

Signed and Sealed this

Nineteenth Day of February 1985

[SEAL]

Attest:

DONALD J. QUIGG

Attesting Officer    Acting Commissioner of Patents and Trademarks